United States Patent [19]

Herold

[11] Patent Number: 4,674,661
[45] Date of Patent: Jun. 23, 1987

[54] CONTAINER FOR DISPENSING DENTAL COMPOSITIONS

[75] Inventor: Wolf-Dietrich Herold, Seefeld, Fed. Rep. of Germany

[73] Assignee: ESPE Stiftung & Co. Produktions- und Vertriebs KG, Seefeld, Fed. Rep. of Germany

[21] Appl. No.: 704,272

[22] Filed: Feb. 22, 1985

[30] Foreign Application Priority Data

Mar. 1, 1984 [DE] Fed. Rep. of Germany ....... 3407648

[51] Int. Cl.⁴ .............................................. B67D 5/40
[52] U.S. Cl. .................................... 222/386; 222/498; 222/528; 222/530; 222/533; 222/556
[58] Field of Search .............. 222/386, 498, 499, 519, 222/526, 527, 528, 529, 531-533, 534-536, 556, 566, 530

[56] References Cited

U.S. PATENT DOCUMENTS

| | | | |
|---|---|---|---|
| 8,709 | 4/1801 | DeRaet et al. | 222/527 |
| 21,556 | 9/1897 | Thurman | 222/527 |
| 1,051,688 | 1/1913 | Cole | 222/536 |
| 2,207,176 | 7/1940 | Phillips | 222/527 X |
| 2,670,885 | 3/1954 | Allen | 222/527 X |
| 2,687,831 | 8/1954 | Miller | 222/527 X |
| 2,701,668 | 2/1955 | Zayan | |
| 2,717,726 | 9/1955 | Mart | 222/536 X |
| 2,727,658 | 12/1955 | Mart | 222/536 X |
| 2,732,736 | 1/1956 | Bonnie | 222/527 X |
| 3,089,626 | 5/1963 | Kubiliunas | 222/536 X |
| 3,251,516 | 5/1966 | Thomas | 222/536 |
| 3,346,147 | 10/1967 | Higgins et al. | 222/386 X |
| 3,863,818 | 2/1975 | Hazard | 222/531 |
| 3,907,106 | 9/1975 | Purrmann | 222/80 |
| 4,272,228 | 6/1981 | Kutik et al. | 222/383 X |
| 4,472,141 | 9/1984 | Dragan | 222/386 X |

FOREIGN PATENT DOCUMENTS

| | | | |
|---|---|---|---|
| 63891 | 11/1982 | European Pat. Off. . | |
| 628404 | 12/1932 | Fed. Rep. of Germany . | |
| 1293627 | 4/1969 | Fed. Rep. of Germany | 222/533 |
| 2110463 | 9/1972 | Fed. Rep. of Germany . | |
| 2644930 | 4/1977 | Fed. Rep. of Germany . | |
| 2741184 | 3/1979 | Fed. Rep. of Germany . | |
| 1493380 | 9/1961 | France | 222/534 |
| 2358334 | 7/1976 | France | 222/527 |
| 253614 | 3/1948 | Switzerland . | |
| 4469 | of 1884 | United Kingdom | 222/527 |
| 428229 | 5/1935 | United Kingdom . | |
| 641233 | 8/1950 | United Kingdom | 222/527 |
| 2005553 | 4/1979 | United Kingdom . | |

*Primary Examiner*—L. J. Paperner
*Assistant Examiner*—P. McCoy Smith
*Attorney, Agent, or Firm*—Schwartz, Jeffery, Schwaab, Mack, Blumenthal & Evans

[57] ABSTRACT

A container suitable for dispensing compositions, particularly dental preparations, has a dispensing tube (14) which constitutes a separate part and is supported for pivotal movement about a pivot axis extending transversely to the longitudinal axis (18) of the container. It is thereby possible to pivot the tube (14) to the operative position most favourable for the respective application, while there is no risk of a cross-sectional constriction or even breakage which might occur on bending. Furthermore, a closing position may be provided in which a bearing member (15) integrally formed with the tube (14) interrupts communication between the tube (14) and the container compartment (10).

11 Claims, 6 Drawing Figures

CONTAINER FOR DISPENSING DENTAL COMPOSITIONS

BACKGROUND OF THE INVENTION

The invention is directed to the dental area and relates to a container for preparing and/or dispensing dental compositions.

Such containers are used especially for producing dental preparations by mixing two or more reactive materials and for dispensing the finished preparation direct at the location to be treated, such as a cavity in a tooth.

U.S. Pat. No. 3,907,106 discloses a container for dispensing dental compositions, which comprises a container body forming a compartment, a piston axially movable in the body and defining a rear end of the compartment, and a dispensing nozzle disposed at a front end of the body. The container as supplied by the manufacturer to the user, for instance the dentist, is charged in such a way that one of the two components to be mixed with each other, which is a powder material, is contained in the mixing compartment and the other, liquid component is contained in a bag disposed beneath a clip which is arranged on the side of the mixing compartment.

In use, the clip is urged transversely of the longitudinal axis of the mixing compartment so that the bag is broken and discharges its content into the interior of the mixing compartment through an opening provided in the mixing compartment wall. Then the container is rapidly reciprocated by means of a shaker in order to react the two components with each other by mixing. Subsequently, the completely mixed dental preparation, which is now ready for use, is dispensed direct at the location to be treated through the nozzle which is integrally formed with the front end of the mixing compartment by pushing the piston in the longitudinal direction of the mixing compartment, after a pin which seals the container during transport, storage and mixing has previously been withdrawn from the front end of the nozzle.

In the known container the nozzle extends in the longitudinal direction of the mixing compartment. Since this position is hardly ever favourable to direct insertion in a dental cavity, it has been found that in practice the assistant will in any case bend the nozzle prior to use by the dentist even if this is not really necessary from the point of view of application. The material of the nozzle wall will thereby be considerably overstretched, which sometimes even results in breakage.

Bending causes a cross-sectional constriction of the nozzle, which in turn leads to segregation of the materials; this is due to the fact that larger material particles pile up in front of the constriction, so that less viscous ingredients are urged through first. Such mixtures, which do not have the proper mixing ratio may be useless and may endanger the success of the dental treatment. Sometimes the dam-up is excessive so that the container becomes completely blocked.

In accordance with the German Laid-Open Application No. 2,741,184 it has been attempted to overcome the already recognized above-mentioned difficulty by making at least the dispensing nozzle, which is integrally formed with the mixing compartment, flexible and surrounding it by a rigid two-part protective cover. Apart from the fact that such a protective cover represents an undesirable increase in the number of parts which must be manufactured and have to be manipulated during application, its provision is impossible with some types of shakers due to the design of the mixing fork thereof. Furthermore, it is difficult with the known container to provide the mixing compartment itself with sufficient rigidity so that it will withstand the pressure applied on dispensing of the finished material by means of the piston, and at the same time to provide the dispensing nozzle integrally formed on the mixing compartment with sufficient flexibility so that the cross-sectional constriction upon bending may be prevented.

From the European Patent Application, Publication No. 63,891, there has been known a mixing and dispensing container for dental preparations, in which the dispensing nozzle is integrally formed with the mixing compartment at an angle to the longitudinal axis of said compartment. Although for a number of applications this position of the nozzle may well be more favourable than the nozzle which conventionally extends in the longitudinal direction of the mixing compartment, there is still the risk that the nozzle will be bent to move it to the respective most suitable position. Besides, this container also cannot be placed in a number of conventional shakers because of the obliquely extending rigid nozzle.

The same problem exists with the container of U.S. Pat. No. 3,907,106 referred to above, in which the nozzle extends axially from the compartment, unless the supporting fork of the shaker is provided with a hole. Apart from this, however, any straight forwardly or obliquely projecting nozzle is disadvantageous, because it substantially increases the overall length of the container and therefore cannot be used with shaking mechanisms protected by a hood which surrounds the supporting fork in relatively close relationship.

With containers of the type described above, in which the nozzle is sealed by a pin until the time of dispensing, there is the additional problem that while the nozzle should be slightly conical throughout its length and funnel-shaped in the entry region for reliable and convenient dispensing, dead spaces will result between the cylindrical pin and the nozzle wall in which the powder component settles during storage and subsequently does not participate in the mixing process. It has been observed that upon dispensing this unmixed material will sit on the strand, so that, unless it is removed, it is inserted first into the dental cavity and cannot properly be cured therein.

It is a general object of the present invention to eliminate at least some of the drawbacks existing with the prior art. As a more specific object, a container suitable for dispensing dental compositions is to be provided which, while consisting of a small number of single parts, allows a variation of the position of the dispensing nozzle without the risk of cross-sectional constrictions.

SUMMARY OF THE INVENTION

To meet with the above object, the container of the present invention comprises a container body forming a compartment for receiving the respective dental composition, a piston axially movable in the body and defining a rear end of the compartment, and a dispensing nozzle disposed at a front end of the body and being formed by a separate part mounted on the body for pivotal movement through a predetermined angular range about a pivot axis that extends transversely to a longitudinal axis of the compartment.

Due to the fact that a separate tube part which forms the nozzle is pivotable it becomes possible to adjust the operative position thereof within a predetermined range in any desired way and also to position the tube in such a way that the container may be inserted into any conventional shaker even if the supporting fork thereof is not provided with a hole. Since the container body and the tube are separately manufactured parts, it is possible to make the container body of relatively rigid material with high dimensional stability as required, among other things, for dispensing the composition by means of the piston, while the tube may have a relatively high elasticity and may be thin-walled, this being favourable for dispensing the composition into very small cavities.

An especially useful range of operative positions, in which the bore of the tube is in communication with the compartment, extends between about 0° and about 50° in terms of the angle formed between the tube and the longitudinal axis of the compartment. Additionally, a rest position outside this operative area, in which the tube extends transversely to the said longitudinal axis, is favourable from the aspect of enabling the container to be used with virtually all conventional types of shakers.

In accordance with a further development of the invention, the tube is curved, preferably in a plane perpendicular to the pivot axis. The range of operative positions of the tube can thus be modified as may be favourable for certain applications.

Further, the tube may be provided on a rotatable bearing member to permit closing the front end of the compartment in the rest position, thereby rendering the conventionally required sealing pin unnecessary. A large and reliable sealing surface is obtained by a bearing member having a circular cross-section, with the center thereof being located on the pivot axis and the tube being eccentrically joined to the bearing member.

In a further embodiment, the bearing member is supported in a bearing surface formed in a front end wall of the body. This concept results in a small number of individual parts required, particularly when the bearing surface is formed in an inner surface of the front end wall, so that the bearing member is supported inside the compartment. On the other hand, forming the bearing surface in an outer surface of the front end wall of the body and retaining the bearing member by a cap which embraces the front end wall may be more advantageous to obtain a reliable seal.

A particularly suitable pivoting range for rest and operative positions is achieved by forming the bearing surface for the bearing member eccentrically with respect to the longitudinal axis of the compartment.

In a further preferred embodiment, the bearing member is provided with a passage continuous with the bore of the tube and having a funnel-shaped inner end. Such a shape permits a smooth flow of the composition to be dispensed independently of the respective operative position.

A further feature of the invention resides in a catch means to define the rest position of the tube relative to the operative range. A perceptable and audible transition between the rest position and the operative range is thus achieved and any inadvertent pivoting of the tube from the sealing position to an operative position or vice versa can be avoided. In a particularly advantageous further development, an abutment means is provided for preventing pivoting of the tube from the operative range to the rest position, which pivoting, if occurring during the dispensing operation, would result in a cross-sectional constriction. Various configurations are available for such catch and abutment means; cooperating integral projections disposed laterally on the tube and in a slot provided in the cap are particularly advantageous as they retain the tube in the cap even before the latter is mounted on the container body, thereby facilitating the assembly.

DESCRIPTION OF THE PREFERRED EMBODIMENTS

Figure 1:
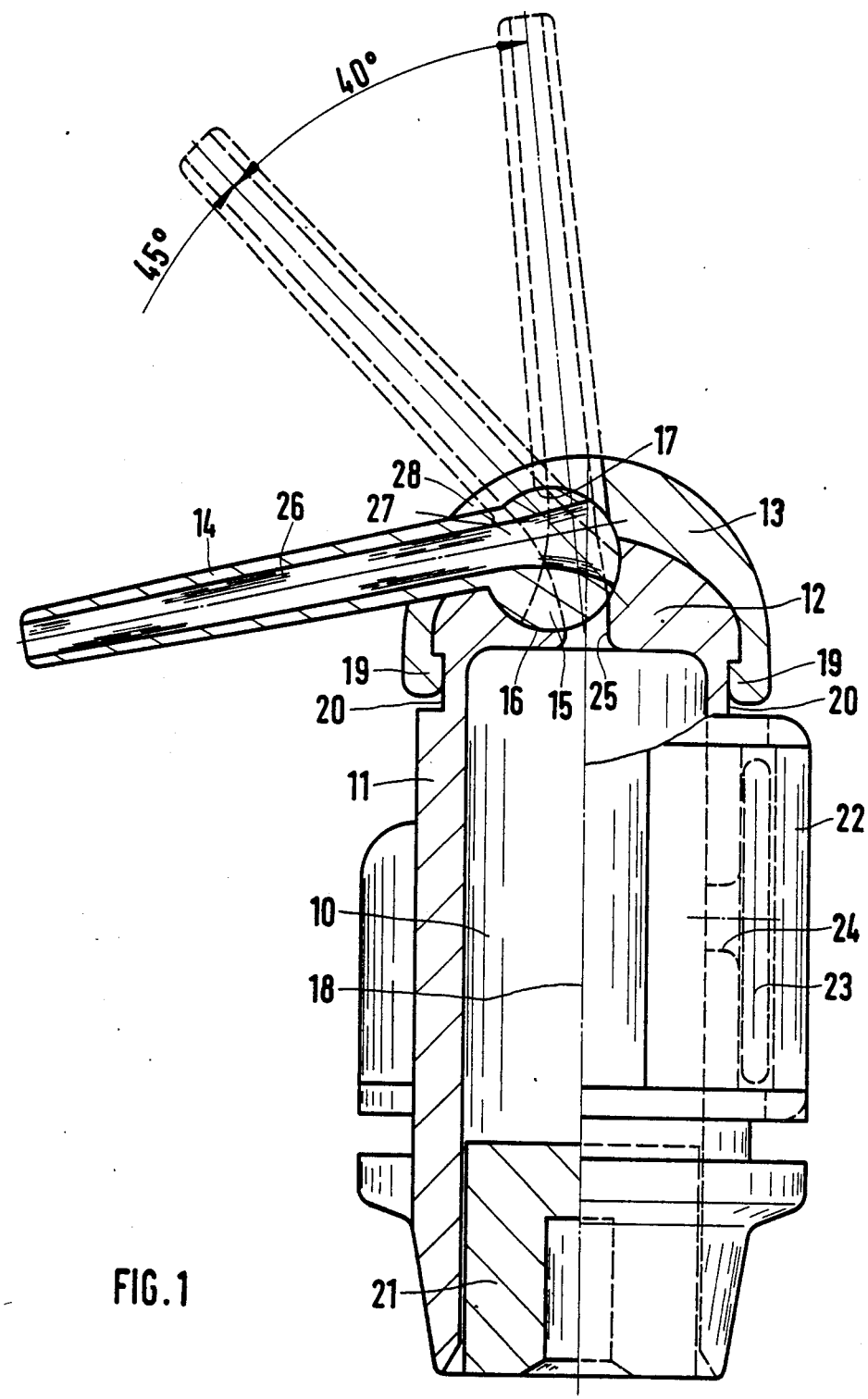
FIG. 1 is a substantially longitudinal section view of a container in the assembled condition.

The container shown in FIG. 1 comprises a container body 11 which constitutes a mixing compartment 10 and includes a forward end wall 12 having a cap 13 in overlapping engagement therewith. A dispensing tube 14, which has a slight conical taper towards its front end, has its rear end integral with a cylindrical bearing member 15, which is held in a bearing shell 16 formed on the outside of the end wall 12 of the container body 11 and in a counter-shell 17 (see also FIG. 3) formed on the inside of the cap 13 and is supported for rotation about its pivot axis which is perpendicular to the longitudinal axis 18 of the mixing compartment 10. At the bottom edge the cap 13 is provided with an inwardly projecting flange 19 which is in resilient engagement with an annular groove 20 formed on the main body 11.

The rear end of the mixing compartment 10 is closed by a piston 21 adapted to be moved forward in the direction of the longitudinal axis 18 for dispensing the composition finished in the mixing compartment 10.

A clip 22, which overlaps about half of the outer wall of the container body 11, is retained by catches (not shown) integrally formed with the container body and contains a foil bag 23 which covers a hole 24 provided in the outer wall of the container body 11. Details relating to the structure and mounting of the clip and the foil bag are described in U.S. Pat. No. 3,907,106, which is incorporated by reference.

In FIG. 1 the tube 14 is illustrated in full lines in its rest position, in which the bearing member 15 closes a bore 25 provided in the end wall 12. Two different operative positions, i.e., the two extreme operative positions, of the tube 14 are illustrated in FIG. 1 in dashed lines; these positions are defined in that a respective inner wall of a passage 27, which is formed in the bearing member 15, merges into the bore 26 of the tube 14 and expands rearwardly in funnel-fashion, is in register with a corresponding wall of the bore 25 in the end wall 12. As indicated in FIG. 1, these two extreme operative positions include a pivot angle of about 40°, wherein the tube in its one operative position extends almost in the direction of the longitudinal axis 18, while in the other position it extends at an angle of about 45° relative to the longitudinal axis 18. In the rest position the tube 14 is pivoted slightly downwardly about an angle of more than 90° to the longitudinal axis 18. The operative range and the rest position may be affected, among other things, by the degree of eccentricity at which the bearing member 15 is disposed relative to the container body 11 or the tube 14 is disposed relative to the bearing member 15, respectively, and by the cross-sectional dimensions of the bore 25 in the end wall 12 and the funnel-like expanded inner end of the passage 27 in the bearing member 15.

Figure 2:
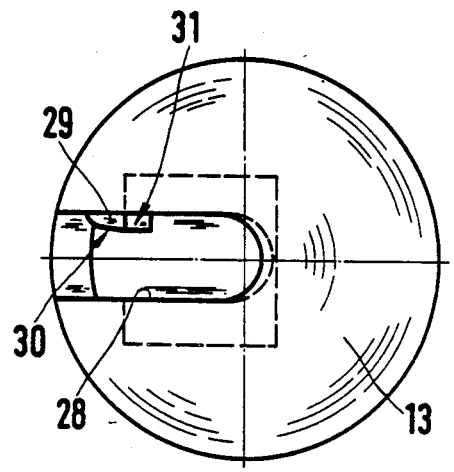
FIG. 2 is a plan view showing the cap of the container of FIG. 1.

The tube 14 extends through a radial slot 28 formed in the cap 13, said slot having an inwardly protruding catch 29 integrally formed on one sidewall thereof. As will be apparent from FIGS. 2 and 3, said catch 29 is provided with a surface 30 continuously rising from the outside towards the centre of the cap, said surface terminating in an abutment 31 which extends perpendicularly to the inner face of the slot 28 and radially to the pivot axis of the bearing member 15. The abutment 31 cooperates with a counter-abutment 32 which in accordance with FIG. 4 is constituted by an integral protrusion 33 provided on the tube 14 immediately outside of the bearing member 15.

Figure 3:
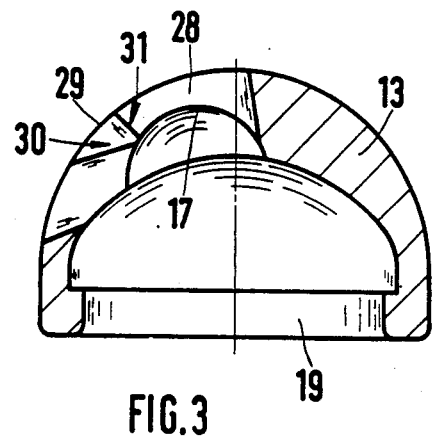
FIG. 3 is a sectional view similar to FIG. 1 through the cap of FIG. 2 only.
Figure 4:
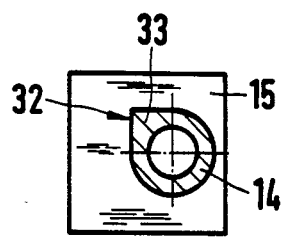
FIG. 4 is a cross-section through the tube slightly above the bearing member formed integrally therewith.

When the tube 14 takes the rest and closing position illustrated in FIG. 1 in full lines, the rearmost portion thereof adjacent the bearing member 15 is disposed in that portion of the slot 28 which according to FIG. 3 is defined by the lower end of the slot and the end of the surface 30.

When the tube 14 is pivoted into the operative area, it has to overcome the catch 29, wherein initially a part of the tube outer wall opposite to the counter-abutment 32 (FIG. 4) comes into engagement with the continuously rising surface 30 of the catch 29. The operative position with maximum pivot relative to the longitudinal axis 18 has been reached when the catch has been overcome, and this may not only be perceived but may also be established by a slight clicking noise. The tube is freely movable within the entire operative range, and the friction of the bearing member is selected such that the tube will remain in the respective predetermined operative position also when the composition is dispensed therefrom. However, any pivoting of the tube from the operative area towards the closed position is prevented by cooperation of the abutment 31 formed on the catch 29 and the counter-abutment 32 provided on the tube 14. It is thereby ensured that the tube is not inadvertently brought into a dispensing position in which the cross-section between the bore 25 in the end wall 12 and the passage 27 in the bearing member 15 is constricted and the above-described segregation might occur.

When the container shown in FIG. 1 is delivered from the manufacturer to the user, it will be charged with two components of a dental composition, one being a powder filled in the mixing compartment 10 and the other one being a liquid contained in the bag 23. The tube 14 will be in the closing position.

To complete the preparation, the clip 22 is first depressed in a direction perpendicular to the longitudinal axis 18 of the mixing compartment 10 so as to break the foil bag 23 and transfer the liquid material through the hole 24 into the mixing compartment 10. Then the container is mounted in a shaker, which is normally provided with a forked support, the two parts of the fork engaging the end face of the cap 13 and the rear side of the container body 11 and of the piston 21. In the rest position the tube 14 will not in any way impede such a mounting.

When the container is removed from the shaker, the composition (for instance a paste) is ready for use. Thereupon the tube 14 may be pivoted to the operative position in which the bore 26 of the tube 14 communicates with the mixing compartment 10 through the passage 27 in the bearing member 15 and the bore 25 in the end wall 12. The tube 14 is pivoted to the respective most suitable operative position, and in this position the container is inserted into a dispensing tool by means of which the piston is pushed forward in order to dispense the finished preparation. Since the tube 14 is made of flexible plastics and of thin-walled design in contrast to the container body 11, which is preferably made of relatively rigid plastics, the preparation may be directly inserted even into small dental cavities.

Figure 5:
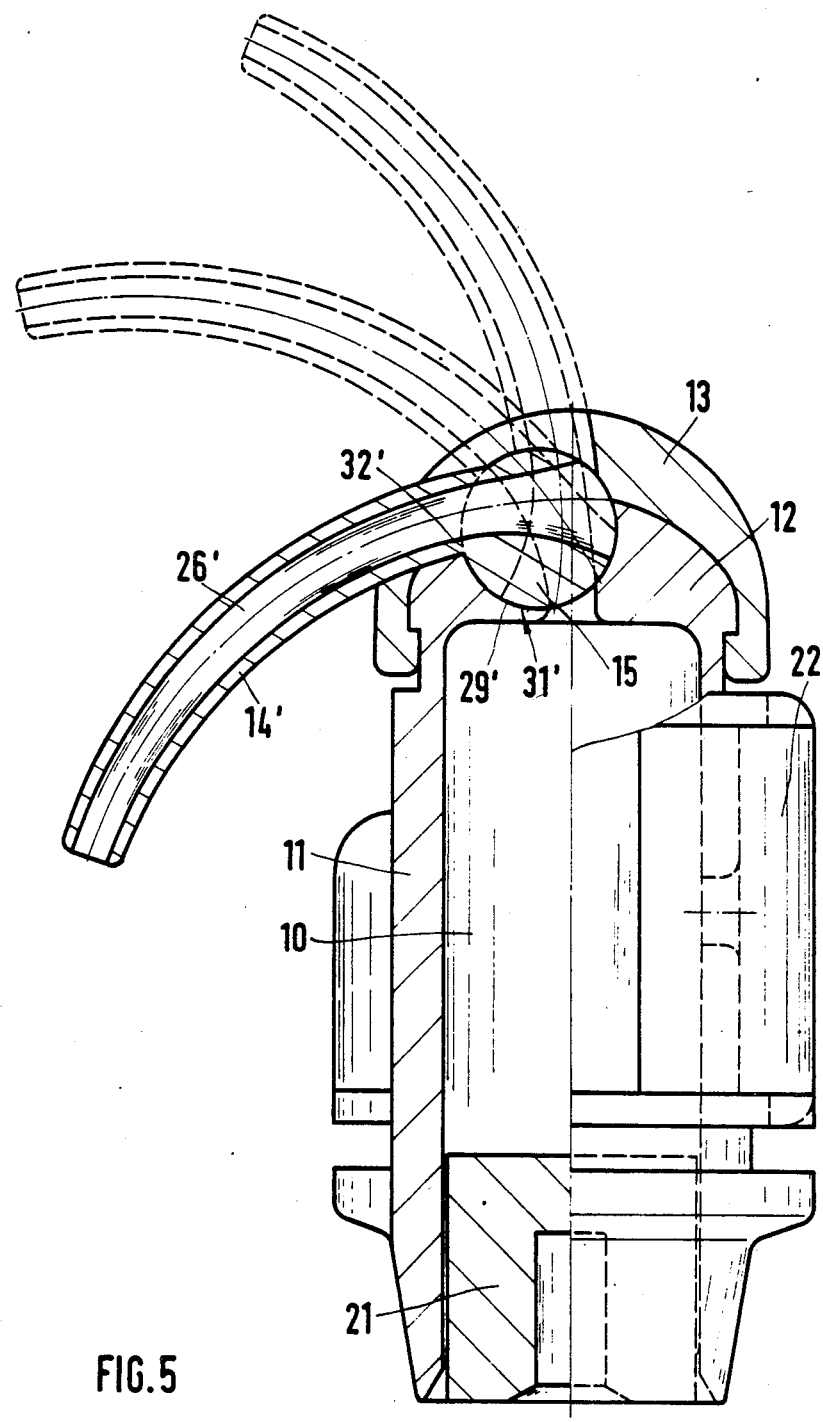
FIG. 5 is a further embodiment of a container in a sectional view similar to that of FIG. 1.

The modification shown in FIG. 5 differs from the embodiment shown in FIG. 1 in that the tube 14' is curved towards the rest position in its plane which is normal to the pivot axis of the bearing member 15. It is thereby possible to achieve still more favourable positions in the operative area for certain applications, while the remaining structure has not been changed. At the same time the extent to which the tube 14' projects laterally is reduced.

A further difference of the modification shown in FIG. 5 resides in the design of the catch 29', which is an eccentric protrusion on the cylinder surface of the bearing member 15 and in the rest position engages a correspondingly eccentric recess in the end wall 12. When the tube 14' is pivoted from the rest position to the operative range, the catch 29' will produce a slightly increasing pressure which decreases abruptly when the tube 14' reaches its operative range in accordance with the central position illustrated in dashed lines in FIG. 5. Any reversal from this position is prevented due to the fact that an abutment 31' of the catch 29' which extends radially to the pivot axis of the bearing member 15 engages a corresponding counter-abutment 32' on the end wall 12.

Figure 6:
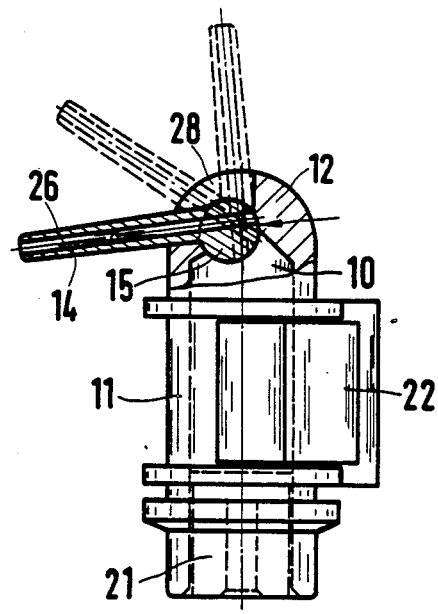
FIG. 6 is another embodiment of the container, again similar to the view of FIG. 1.

The embodiment shown in FIG. 6 differs from that shown in FIG. 1 mainly in that the bearing member 15 engages the end wall 12 from the inside of the mixing compartment 10. In this case the cap 13 provided in FIGS. 1 and 5 may be omitted.

The invention has been explained above with reference to embodiments thereof which relate to a dual-component mixing container, wherein one of the two components is provided in a compartment disposed laterally of the container body. The invention is of course also applicable with other mixing container designs for two- or multicomponent preparations and also for pure dispensing containers that may, for instance, contain an immediately ready photopolymerizable dental composition.

Furthermore it has been explained that the tube is pivotable between a closing position and an operative range and also within the operative range. The invention is also applicable when no closing position is provided or when a single operative position is sufficient for certain applications.

What is claimed is:

1. A container for mixing and dispensing dental compositions, comprising
   (a) a container body having a longitudinal axis and forming a compartment for receiving a first dental composition, said body having a front end wall formed with a bearing surface positioned eccentrically with respect to said longitudinal axis, (b) means for containing and supplying a separate second dental composition to said compartment to permit mixing of said compositions to form a dispensable material, (c) a piston axially movable in said body to dispense said mixed material, said piston defining the rear end of said compartment, (d) a separately formed dispensing nozzle having a bore extending therethrough for dispensing said mixed material, said bore being adapted to communicate with said compartment when material is to be dispensed, (e) said nozzle having a rear end eccentrically mounted on a bearing member said bearing member being mounted on said bearing surface formed in said front end wall of said body, said bearing member being generally circular in cross-section with the center thereof forming the pivot axis for said nozzle, said pivot axis being generally transverse to and horizontally spaced from the longitudinal axis of said body, said bearing member having a bore aligned with the bore of said nozzle for selective communication with said compartment, (f) a separately formed cap secured to and covering said front end wall to sealably mount said bearing member on said front end wall, said cap being formed with a radial slot to receive said nozzle, the length of said slot being such that said nozzle can be pivoted through a predetermined angular range about the pivot axis of said bearing member, whereby the bore of said nozzle can be pivoted from a rest position where the bores of said nozzle and bearing member are sealed from said compartment, in which rest position the nozzle extends generally transversely to said longitudinal axis, to an operative angular range of positions in which said bores are in communication with said compartment to permit said mixed material to be dispensed, with the eccentric mounting of said bearing member on said bearing surface and said nozzle on said bearing providing tight sealing in all operative ranges of movement of said nozzle.

2. The container of claim 1, wherein said operative range is between 0° and about 50°, relative to the longitudinal axis, the bore of said nozzle being in communication with said compartment within said operative area.

3. The container of claim 1, wherein said nozzle is curved.

4. The container of claim 3, wherein said nozzle is curved in a plane perpendicular to said pivot axis.

5. The container of claim 1, wherein the bore of said bearing member includes a funnel-shaped inner end and an outer end which merges into the bore of said nozzle.

6. The container of claim 1, further comprising catch means defining said rest position of said nozzle relative to said operative range.

7. The container of claim 6, wherein said catch means is formed by cooperating integral projections disposed laterally on the nozzle and in said radial slot.

8. The container of claim 7, wherein said catch means further comprises abutment means for preventing pivoting of said nozzle from said operative range to said rest position.

9. The container of claim 8, wherein said abutment means comprises cooperating integral projections disposed laterally on said nozzle and in said slot.

10. The container of claim 1, wherein said body and nozzle are made of different plastics materials.

11. The container of claim 10, wherein said body is made of a more rigid plastics material and said nozzle has a thin wall molded of a more elastic plastics material.

* * * * *